(12) United States Patent
Simoulidis et al.

(10) Patent No.: US 7,175,835 B1
(45) Date of Patent: *Feb. 13, 2007

(54) COSMETIC EMULSIONS WITH INORGANIC SUNSCREENS STABILIZED WITH CONJUGATED LINOLEIC ACID

(75) Inventors: Sofia Simoulidis, Norwalk, CT (US); Jeffrey William Rosevear, Wallingford, CT (US); Brian John Dobkowski, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/318,130

(22) Filed: Dec. 23, 2005

(51) Int. Cl.
*A61Q 17/04* (2006.01)
*A61K 8/00* (2006.01)
*A61K 8/06* (2006.01)
*A61K 31/19* (2006.01)

(52) U.S. Cl. .................. 424/59; 424/60; 424/400; 424/401; 514/557; 514/844; 514/847; 514/937; 514/938; 514/969

(58) Field of Classification Search .............. 424/59, 424/60, 400, 401; 514/844, 847, 937, 938, 514/969, 557
See application file for complete search history.

(56) References Cited

U.S. PATENT DOCUMENTS

| | | | |
|---|---|---|---|
| 5,188,831 A | 2/1993 | Nicoll et al. | |
| 5,215,749 A | 6/1993 | Nicoll et al. | |
| 5,422,371 A | 6/1995 | Liao et al. | |
| 5,541,405 A | 7/1996 | Hassler, Jr. et al. | |
| 5,723,139 A | 3/1998 | Granger et al. | |
| 5,759,556 A | 6/1998 | Burger et al. | |
| 6,019,990 A | 2/2000 | Remmereit | |
| 6,171,581 B1 * | 1/2001 | Joshi et al. | 424/65 |
| 6,287,553 B1 | 9/2001 | Alaluf et al. | |
| 6,403,064 B1 | 6/2002 | Alaluf et al. | |
| 6,524,598 B2 | 2/2003 | Sunkel et al. | |
| 6,551,602 B1 | 4/2003 | Barrett et al. | |
| 6,645,502 B2 * | 11/2003 | Sandewicz et al. | 424/195.15 |
| 6,696,049 B2 | 2/2004 | Vatter et al. | |
| 6,953,583 B1 | 10/2005 | Ghisalberti | |
| 2003/0003068 A1 | 1/2003 | Mayes et al. | |
| 2005/0118208 A1 | 6/2005 | Bewert et al. | |
| 2005/0163730 A1 | 7/2005 | Rosevear et al. | |

FOREIGN PATENT DOCUMENTS

| | | |
|---|---|---|
| EP | 0 742 005 B1 | 4/1996 |
| EP | 0 803 247 B1 | 4/1997 |
| FR | 2 780 886 | 7/1998 |
| WO | 98/13020 | 4/1998 |
| WO | 99/26588 | 6/1999 |
| WO | 01/08650 A1 | 2/2001 |

\* cited by examiner

*Primary Examiner*—Shelley A. Dodson
(74) *Attorney, Agent, or Firm*—Milton L. Honig

(57) ABSTRACT

A cosmetic water-in-oil composition is provided which includes a water-in-oil emulsifying silicone surfactant, an ultrafine titanium dioxide and conjugated linoleic acid. The presence of conjugated linoleic acid stabilizes the composition against color degradation and also maintains an approximately steady viscosity.

9 Claims, No Drawings

COSMETIC EMULSIONS WITH INORGANIC SUNSCREENS STABILIZED WITH CONJUGATED LINOLEIC ACID

BACKGROUND OF THE INVENTION

1. Field of the Invention

The invention concerns cosmetic emulsion compositions formulated with inorganic sunscreens stabilized against color and viscosity degradation.

2. The Related Art

Sunscreen compositions are commonly used during outdoor work or leisure. They protect exposed skin against sunburn, cancer and even photoaging. In general, sunscreen preparations are formulated as creams, lotions or oils containing as active agent an ultraviolet radiation absorbing or at least reflecting chemical compound.

The ideal sunscreen formulation should be non-toxic, non-irritating to skin tissue and capable of convenient application in a uniform continuous film. The sunscreen active agent as well as the composition into which it is formulated should be sufficiently chemically and physically stable. An acceptable shelf life is required for extended storage.

Chromophoric organic sunscreen agents are generally the most effective. Unfortunately many of these organic actives cause adverse allergic reactions. It is therefore desirable to minimize the level of such materials.

Inorganic ultrafine particulate compounds such as zinc oxide and titanium dioxide have been employed as sunscreen agents. Illustrations of this technology are found in U.S. Pat. No. 5,215,749 and U.S. Pat. No. 5,188,831, both to Nicoll et al. Inorganics are not known as sensitizers generating allergic reactions. However, stability of such formulations is a noticeable problem. Adverse effects include viscosity buildup and discoloration under extended storage conditions. These adverse consequences can be particularly pronounced in emulsions which are of the oil continuous variety.

Accordingly, there remains a need to uncover inorganic sunscreen particulate containing formulations of increased storage stability, particularly compositions resistant to significant changes in viscosity and color.

SUMMARY OF THE INVENTION

A cosmetic composition is provided which is a water-in-oil emulsion including:
(i) from about 0.1 to about 30% by weight of a water-in-oil emulsifying silicone surfactant;
(ii) from about 0.1 to about 30% by weight of a titanium dioxide sunscreen agent; and
(iii) from about 0.1 to about 10% of a conjugated linoleic acid.

DETAILED DESCRIPTION OF THE INVENTION

Now it has been found that a water-in-oil cosmetic composition containing conjugated linoleic acid can impart both viscosity and color stability to formulations containing sunscreen grade titanium dioxide particulates. Ordinarily unsaturated compounds, of which CLA is an example, would themselves be expected to be unstable and color body producing. It was therefore surprising to note that CLA had the exact opposite effect in oil continuous emulsions that suspended titanium dioxide. Only small amounts of CLA were needed to achieve the stabilization results.

Conjugated Linoleic Acid

Conjugated linoleic acid (hereinafter referred to also as CLA) comprises a group of positional and geometric isomers of linoleic acid in which various configurations of cis and trans double bonds at positions (6,8), (7,9), (8,10), (9,11), (10,12) or (11,13) are possible. Thus, twenty-four different isomers of CLA exist.

The invention also includes derivatives of the free acid which thus comprise conjugated linoleic acid moieties. Preferable derivatives include those derived from substitution of the carboxyl group of the acid, such as esters (e.g. retinyl esters, triglyceride esters, monoglyceride esters, diglyceride esters, phosphoesters), amides (e.g. ceramide derivatives), salts (e.g. alkali metal and alkali earth metal salts, ammonium salts); and/or those derived from substitution of the $C_{18}$ carbon chain, such as alpha hydroxy and/or beta hydroxy derivatives.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

Wherever the term "conjugated linoleic acid" or "CLA" is used in this specification it is to be understood that the derivatives thereof comprising CLA moieties are also included. "CLA moieties" refers to CLA fatty acyl portion(s) of a CLA derivative.

The isomers of greatest interest in the present cosmetic compositions are cis 9, trans11-linoleic acid and trans10, cis12-linoleic acid. Hereinafter the term "9,11-linoleic" or "10,12-linoleic" shall mean preferentially these two main isomers, but will include lesser amounts of the remaining isomers, particularly when obtained or derived from a natural source.

In accordance with the present invention, 9,11-linoleic acid and 10,12-linoleic acid are formulated into cosmetic preparations either as the free acid, as individual chemical derivatives, or as combinations of free acid and derivative.

By "c9, t11 and t10, c12 isomer enriched CLA" is meant that at least 30% by weight of the total CLA (and/or CLA moieties) present in the composition is in the form of the cis 9, trans 11 and trans 10, cis 12 isomers. Preferably, at least 40%, most preferably at least 50%, by weight of the total CLA and/or CLA moieties present in the composition, is in the form of the aforementioned isomers.

Amount of the CLA present in emulsions of this invention may range from about 0.1 to about 10% by weight of the composition. More preferably the amount is from about 0.5% to about 5%, and most preferably from about 1% to about 3%.

Mixed isomers of CLA are prepared by high temperature alkali treatment of Safflower oil, generating CLA with equal amounts of the c9, t11 and t10, c12 CLA isomers. CLA enriched in the c9, t11 CLA is separated from the mix by selective esterification with lauryl alcohol using *Geotrichum Candidum* as a catalyst. The enriched c9, t11 CLA is hydrolyzed and converted to the triglyceride. After the esterification step and separation the remaining CLA free acids are enriched in t10, c12 CLA.

Commercially CLA is available as Clarinol® A-80 and A-95 from Loders-Croklaan, Channahon, Ill. and Neobee® CLA 80 and 90 from Stepan, North Field, Ill.

Water-in-Oil Surfactant

A wide variety of silicone surfactants are useful herein. These silicones are typically organically modified organopolysiloxanes such as dimethicone copolyols.

Nonlimiting examples of dimethicone copolyols and other silicone surfactants useful herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this latter material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate sold under the tradename ABIL® WS-08 (also available from Goldschmidt). Other nonlimiting examples of dimethicone copolyols include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, dimethicone copolyol sulfosuccinate and dimethicone copolyol stearate. Most preferred is PEG-10 Dimethicone available from Shin Etsu.

Amounts of the silicone surfactant may range from about 0.1 to about 30%, preferably from about 1 to about 10%, optimally from about 1.5 to about 5% by weight of the composition.

Titanium Dioxide Particles

Compositions of this invention will contain ultrafine titanium dioxide in a form which may either be a water-dispersible or an oil-dispersible form. By a "ultrafine titanium dioxide" is meant titanium dioxide having an average particle size of less than 100 nm, preferably from about 90 to about 1 nm, more preferably from about 60 to about 5 nm, even more preferably from about 30 to about 10 nm, and optimally from about 25 to about 15 nm.

Water-dispersible titanium dioxide is an ultrafine titanium dioxide the particles of which are uncoated or which are coated with a material to impart a hydrophilic surface property to the particles. Examples of such materials include aluminum oxide, silica and aluminum silicate.

Oil-dispersible titanium dioxide is ultrafine titanium dioxide, the particles of which exhibit a hydrophobic surface property, and which for this purpose can be coated with hydrophobic materials including metal soaps such as aluminum stearate, aluminum laurate or zinc stearate, or with organosilicone compounds such as dimethicones and dimethiconols. Other useful coatings include polyols such as butylenes glycol, polyethylene glycol and glycerin; natural and synthetic esters including castor oil, caprylic/capric triglyceride, octyl dodecyl neopentanoate, isopropyl myristate, octyl palmitate, $C_{12}$–$C_{15}$ alkyl benzoate and mixtures thereof and combinations of organic liquids with inorganic powders. Most preferred are the oil-dispersible titanium dioxides.

Amounts of the titanium dioxide sunscreen agent may range from about 0.1 to about 30%, preferably from about 0.5 to about 15%, more preferably from about 1 to about 10% by weight of the composition.

Dispersed Aqueous Phase

The compositions of the present invention comprise from about 5% to about 90%, more preferably from about 30% to about 75%, and even more preferably from about 45% to about 60% of a dispersed aqueous phase. In emulsion technology, the term "dispersed phase" means that the phase exists as small particles or droplets suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, and colorants.

Optional Components

The composition of the present invention may contain a variety of other ingredients that are conventionally used in given product types provided that they do not unacceptably alter the benefits for the invention.

A component of the present invention may be a crosslinked silicone (organopolysiloxane) elastomer. No specific restriction exists as to the type of curable organopolysiloxane composition that can serve as starting material for the crosslinked silicone elastomer. Examples in this respect are addition reaction-curing organopolysiloxane compositions which cure under platinum metal catalysis by the addition reaction between S1H-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and S1H-containing diorganopolysiloxane; condensation-curing organopolysiloxane compositions which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

an organopolysiloxane having at least 2 lower alkenyl groups in each molecule;

an organopolysiloxane having at least 2 silicon-bonded hydrogen atoms in each molecule; and a platinum-type catalyst.

The crosslinked siloxane elastomer may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxane compositions available under the INCI names of dimethicone/vinyl dimethicone crosspolymer, dimethicone crosspolymer and Polysilicone-11. Ordinarily these materials are provided as a 1–30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15,16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silesquioxane crosspolymers from Shin Etsu sold as KSP-100, KSP-101, KSP-102, KSP-103, KSP-104, KSP-105, and hybrid silicone powders that contain a fluoroalkyl group or a phenyl group sold by Shin Etsu as respectively KSP-200 and KSP-300. Also of use is Dow Corning 5-7070, a silicone amino elastomer emulsion with INCI name of silicone quaternium-16/glycidoxy dimethicone crosspolymer (and) trideceth-12.

The crosslinked silicone elastomers may range in concentration from about 0.01 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products 9040 and 9045. For instance, the amount of crosslinked silicone elastomer in 9040 and 9045 is between 12 and 13% by weight.

Most preferred as the silicone elastomer is DC 9045 which has a D5 cyclomethicone swelled elastomer particle size (based on volume and calculated as spherical particles) which averages about 38 micron, and may range from about 25 to about 55 micron.

The compositions may include from about 1% to about 80%, by weight of the composition, of a suitable carrier for the crosslinked organopolysiloxane elastomer component described above. The carrier, when combined with the cross-linked organopolysiloxane elastomer particles serves to suspend and swell the elastomer particles to provide an elastic, gel-like network or matrix. The carrier for the crosslinked siloxane elastomer is liquid under ambient conditions, and preferably has a low viscosity to provide for improved spreading on the skin.

Concentrations of the carrier may range from about 5% to about 60%, more preferably from about 5% to about 40%, by weight of the composition.

These liquid carriers may be organic, silicone-containing or fluorine-containing, volatile or non-volatile, polar or non-polar, provided that the liquid carrier forms a solution or other homogeneous liquid or liquid dispersion with the selected cross-linked siloxane elastomer at the selected siloxane elastomer concentration at a temperature of from about 28° C. to about 250° C., preferably from about 28° C. to about 78° C. The term "non-polar" typically means that the material has a solubility parameter below about 6.5 $(cal/cm^3)^{0.5}$.

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Examples of preferred non-polar, volatile hydrocarbons include polydecanes such as isododecane and isodecane (e.g., Permethyl-99A which is available from Presperse Inc.) and the C7–C8 through C12–C15 isoparaffins (such as the Isopar Series available from Exxon Chemicals). Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp).

Compositions of the present invention may also contain $C_1$–$C_{20}$ alpha- and beta-hydroxy carboxylic acids and salts thereof. The salts are preferably alkaline metal, ammonium and $C_1$–$C_{12}$ alkanolammonium salts and mixtures thereof. The term "alpha-hydroxycarboxylic acids" includes not only hydroxy acids but also alpha-ketoacids and related compounds of polymeric forms of hydroxyacid.

Alpha-hydroxyacids are organic carboxylic acids in which one hydroxyl group is attached to the alpha carbon adjacent the carboxy group. The generic structure is as follows:

(R*a*)(R*b*)C(OH)COOH where Ra and Rb are H, F, Cl, Br, alkyl, aralkyl or aryl group of saturated or unsaturated, isomeric or non-isomeric, straight or branched chain or cyclic form, having 1 to 25 carbon atoms, and in addition Ra and Rb may carry OH, CHO, COOH and alkoxy groups having 1 to 9 carbon atoms.

The alpha-hydroxyacids may be present as a free acid or in lactone form, or in a salt form with an organic base or an inorganic alkali. The alpha-hydroxyacids may exist as stereoisomers as D, L, and DL forms when Ra and Rb are not identical.

Typical alkyl, aralkyl and aryl groups for Ra and Rb include methyl, ethyl, propyl, isopropyl, butyl, pentyl, octyl, lauryl, stearyl, benzyl and phenyl. Most preferred among the alpha-hydroxyacids are glycolic acid, lactic acid, alpha-hydroxycaprylic acid, gluconolactone and combinations thereof.

Among the beta-hydroxycarboxylic acids, the most prominent and useful is salicylic acid.

Amounts of the hydroxy carboxylic acids may range from about 0.01 to about 15%, preferably from about 0.1 to about 12%, more preferably from about 1 to about 8%, optimally from about 2 to about 8% by weight of the total cosmetic composition.

Humectant may be incorporated into compositions of the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, 2-methyl-1,3-propanediol, ethoxylated glycerol, propoxylated glycerol and mixtures thereof. Amounts of the humectant may range from about 0.01 to about 30%, preferably from about 0.1 to about 15%, optimally from about 2 to 10% by weight of the composition.

Emollients may be formulated into the compositions. These emollients may be selected from hydrocarbons, silicones, fatty alcohols, fatty acids, synthetic or natural esters and combinations thereof. Amounts of the emollients may range from about 0.01 to about 30%, preferably from about 0.1 to about 10%, optimally from about 0.5 to about 5% by weight of the composition.

Hydrocarbons encompass mineral oil, polyalphaolefins and isoparaffins.

Among the ester emollients are:

Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.

Ether-esters such as fatty acid esters of ethoxylated fatty alcohols.

Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

Wax esters such as beeswax, spermaceti, myristyl myristate, stearyl stearate.

Mono-, Di- and Triglyceride esters such as PEG-8 caprylic/capric triglyceride.

Sterols esters, of which cholesterol fatty acid esters are examples thereof.

Most preferred is glycerol monostearate available from Kessco Corporation and Sterols sold under the trademark Generol 122®.

Natural esters which may be employed as emollients include olive oil, sunflower seed oil, safflower oil, cotton seed oil, rape seed oil, palm kernel oil, palm oil and mixtures thereof.

Fatty alcohols may also serve as emollients. These are typically formed from 10 to 30 carbon atoms and include cetyl, myristyl, palmityl, stearyl, isostearyl, hydroxystearyl, oleyl, linoleyl, behenyl alcohols and mixtures thereof.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids. Amounts may range from about 0.1 to about 20%, preferably from about 1 to about 10%, optimally from about 2 to about 5% by weight.

The compositions of the present invention may comprise a skin lightening agent. When used, the compositions preferably comprise from about 0.1% to about 10%, more preferably from about 0.2% to about 5% by weight of the composition, of a skin lightening agent. Suitable skin lightening agents include niacinamide, kojic acid, arbutin, tranexamic acid, ethyl resorcinol, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Most preferred is iodopropynyl butylcarbamate available from Lonza Corporation under the trademarks Glydant Plus and Glycasil L. Preservatives are preferably employed in amounts ranging from 0.001% to 2% by weight of the composition.

Compositions of the present invention may further include herbal extracts. Illustrative extracts include Centella Asiatica, Ginseng, Citrus Unshui, Ginko Biloba, Chamomile, Green Tea, Scullcap, Nettle Root, *Swertia Japonica*, Fennel and Aloe Vera extracts and combinations thereof. Amounts of each of the extracts on an actives basis may range from about 0.00001 to about 1%, preferably from about 0.001 to about 0.5%, optimally from about 0.005 to about 0.2% by weight of the composition.

Minor adjunct ingredients may also be present in the compositions. Among these may be vitamins such as Vitamin E esters, Vitamin C, Panthenol and any of the Vitamin B complexes (e.g. niacinamide and Vitamin B6). Retinoids may be employed including retinol, retinyl linoleate, retinyl acetate, retinoic acid and combinations thereof. Anti-irritant agents may also be present including those of steviosides, alpha-bisabolol and glycyhrizzinate salts. Each vitamin, retinoid or anti-irritant agent may be present in amounts ranging from about 0.0001 to about 1.0%, preferably from about 0.001 to about 0.5%, optimally from about 0.01 to about 0.3% by weight of the composition.

The cosmetic compositions can exhibit pH properties ranging from pH 2 to 10. A preferred embodiment has pH ranging from about 4.5 to about 7.0.

The compositions of the present invention can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon—carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaeryriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyidimethyl Taurate (e.g. Simulgel® NS and INS 100), Acrylate/Sodium Acryloyldimethyl Taurate (e.g. Simulgel® EG), Sodium Acryloyidimethyl Taurate (e.g. Simulgel® 800) and Ammonium Acryloyldimethyl Taurate/Vinyl Pyrrolidone (e.g. Aristoflex® AVC).

c. Polyacrylamide Polymers

The compositions of the present invention can optionally comprise polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, aga, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

Another optional ingredient may be an organic sunscreen agent. Sunscreen agents have at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl)(6-propyl piperonyl)ether; Hydroquinone; Benzophenones(Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyidimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, 4-methylbenzylidene camphor, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, terephthalidene dicamphor sulfonic acid and mixtures thereof. Amounts may range from about 0.1 to about 10%, preferably from about 1 to about 5% by weight of the composition.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE I–V

A series of sunscreen formulations according to the present invention are reported in these Examples. The resultant creams have the following components.

| Component | I | II | III | IV | V |
|---|---|---|---|---|---|
| Phase A | | | | | |
| Deionized Water | Qs | Qs | Qs | Qs | Qs |
| Phase B (Surfactant Network) | | | | | |
| NET-WO (PEG-10 Dimethicone & Disteardimonium Hectorite & Cyclopentasiloxane) | 1.8000 | 1.8000 | 1.8000 | 1.8000 | 1.8000 |
| PEG-10 Dimethicone | 1.6000 | 1.6000 | 1.8000 | 1.8000 | 1.8000 |
| Phase C (Humectant/Emollient) | | | | | |
| Glycerin | 10.0000 | 12.0000 | 12.0000 | 14.0000 | 9.0000 |
| Caprylic/Capric Triglycerides | 3.0000 | 3.0000 | 3.0000 | 3.0000 | 3.0000 |
| Phase D (Sunscreen) | | | | | |
| Titanium Dioxide | 6.0000 | 6.0000 | 6.0000 | 6.0000 | 6.0000 |
| Phase E (Silicone) | | | | | |
| DC 9045 (Dimethicone Crosspolymer and Cyclopentasiloxane) | 26.0000 | 26.0000 | 26.0000 | 26.0000 | 26.0000 |
| Phase F | | | | | |
| Clarinol ® A-80 (Conjugated Linoleic Acid) | 0.5000 | 0.5000 | 1.0000 | 1.0000 | 1.3000 |
| Herbal Extracts/Nutrients* | 2.0000 | 2.0000 | 2.0000 | 2.0000 | 2.0000 |
| Phase G (Fragrance/Anti-Oxidant/Preservative) | | | | | |
| Fragrance | 0.3500 | 0.3500 | 0.3500 | 0.3500 | 0.3500 |
| Disodium EDTA | 0.0500 | 0.0500 | 0.0500 | 0.0500 | 0.0500 |
| Glydant Plus Liquid (DMDM Hydantoin and Iodopropynyl Butylcarbamate) | 0.2000 | 0.2000 | 0.2000 | 0.2000 | 0.2000 |

*Includes: Vitamin E Acetate, Vitamin A Palmitate, Ceramide 3 and 6, Bisabolol, Borage Oil, Coriander Seed Oil, Sodium Lactate, Sodium Ascorbyl Phosphate, Betula Alba Extract (White Birch), DL-Panthenol, Sodium PCA (50%), Hydrolyzed Milk Protein, Pomegranate Extract, Cholesterol and Stearic Acid.

EXAMPLE VI

A series of color stability experiments were conducted to evaluate the effect of CLA in preventing discoloration upon aging of oil continuous emulsions. The following Table details components of the four compositions (A–D) employed for this study.

| | Composition (Weight %) | | | |
|---|---|---|---|---|
| Component | A | B | C | D |
| Dimethicone Crosspolymer (DC 9045 ®) | 26.00 | 26.00 | 26.00 | 26.00 |
| Glycerin | 10.00 | 10.00 | 10.00 | 10.00 |
| Parsol MCX ® (Ethylhexylmethoxy Cinnamate) | 6.00 | 6.00 | 6.00 | 6.00 |
| Caprylic/Capric Triglycerides | 3.00 | 3.00 | 3.00 | 3.00 |
| Zinc Oxide or Titanium Dioxide | 2.00 | 2.00 | 2.00 | 2.00 |
| NET-WO (PEG-10 Dimethicone & Disteardimonium Hectorite & Cyclopentasiloxane) | 1.80 | 1.80 | 1.80 | 1.80 |
| PEG-10 Dimethicone | 0.60 | 0.60 | 0.60 | 0.60 |
| Timiron MP-111 ® | 0.50 | 0.50 | 0.50 | 0.50 |
| Herbal Extracts and Other Nutrients** | 2.08 | 2.08 | 2.08 | 2.08 |
| Disodium EDTA | 0.05 | 0.05 | 0.05 | 0.05 |
| Glydant Plus Liquid ® | 0.20 | 0.20 | 0.20 | 0.20 |
| Conjugated Linoleic Acid* | 0.00 | 1.00 | 2.00 | 3.00 |
| Disodium EDTA | 0.05 | 0.05 | 0.05 | 0.05 |
| Glydant Plus Liquid ® | 0.20 | 0.20 | 0.20 | 0.20 |
| Water | qs | qs | qs | qs |

*37% c9, t11 and 38% t10, c12 linoleic acid isomer mixture
**Herbal Extracts/Nutrients included only in the Zinc Oxide formulas.

Color Comparison Test

Color was evaluated by the Hunter Lab method. Intrinsic optical properties of the formulas were tested using a Hunter Lab LabScan XE (Hunter Associates Laboratory, Inc. Reston, Va.) using a standard sample cup port plate. The equipment settings used were:
  Spectral Performance:
    Wavelength Range: 400–700 nm
    Wavelength Internal: 10 nm
    Bandpass: 10 nm equivalent triangular
    Photometric Range: 0–150%

The LabScan XE 0/45 spectrophotometer in the port-up orientation is then configured for a 1.75-inch area of view with UV filter set to nominal. Once the instrument is standardized following the procedure specified in the instrument manual and commercially supplied computer software the sample is prepared for color (a*, b*, and L*) measurement.

The black plastic ring is placed within the sample cup that is then filled with product to a level above the ring. The ceramic disk is then placed on top of the sample with the white portion facing the sample until it rests firmly on top of the plastic ring. This disk provides a white background to direct light that has traveled through the sample back to the detector. The goal is to have the sample appear smooth and opaque through the bottom of the sample cup. Next, the sample is placed on the sample cup port plate and covered with the opaque cover. This cover provides a light trap to exclude interference of external light on the sample measurements. The average of three readings is used for a single color measurement representing the color of the batch. The color lab is presented by the Hunter lab color space a*, b*, and L*. Term a* is green-red space, term b* is blue-yellow space, and term L* is black-white space. For example, a large L* value means more white, and smaller b* value means more blue. The overall color difference from the standard sample is then determined by the value of dE*. dE* can be obtained by configuring the instrument to display it when specifying your settings or it can be calculated as follows:

$$dE^* = \sqrt{(dL)^2 + (da)^2 + (db)^2}$$

where:
dL=$L^*_{sample} - L^*_{reference\ sample}$
da=$a^*_{sample} - a^*_{reference\ sample}$
db=$b^*_{sample} - b^*_{reference\ sample}$ The greater the value of dE, the greater the degree of color change from the control. Conversely, low values of dE indicate that the overall color of the sample is closer to that of the control.

RESULTS

Results of the color study are reported in the Tables below.

Formula with Zinc Oxide

| Sample | CLA Content (%) | dE Value* |
|---|---|---|
| A | 0 | 0.74 |
| B | 1.0 | 1.21 |
| C | 2.0 | 2.78 |
| D | 3.0 | 3.63 |

*Results are reported for formulas held for 2 months at 43° C. Changes in the dE Value are relative to the 0% CLA formula stored at 22° C. for 2 months.

Formula with Titanium Dioxide

| Sample | CLA Content (%) | dE Value* |
|---|---|---|
| A | 0 | 0.654 |
| B | 1.0 | 0.147 |
| C | 2.0 | 0.163 |
| D | 3.0 | 0.281 |

*Results are reported for formulas held for 1 month at 50° C. Changes in dE Value are relative to the 0% CLA formula stored at 4° C. for 1 month.

In the presence of zinc oxide, addition of CLA resulted in an ever increasing color problem. By comparison, replacement of zinc oxide with titanium dioxide resulted in a stable formula, wherein CLA prevented discoloration.

EXAMPLE VII

Another property manifesting stability is that of viscosity. Sunscreen compositions with zinc oxide were compared to identical ones where titanium dioxide replaced the zinc oxide. These compositions are reported in the Table at Example VI.

The compositions were placed on storage for a period of one month at 50° C. Viscosities were measured using a Brookfield RVT viscometer at 23° C., Spindles T(-B, -C or -E) at 5 rpm. Results are recorded in the Tables below.

Formula with Zinc Oxide

| | | % Viscosity Change | |
|---|---|---|---|
| Sample | CLA Content (%) | 1 month | 2 months |
| A | 0 | 33.64 | 38.44 |
| B | 1.0 | 82.48 | 83.97 |
| C | 2.0 | 318.86 | 342.98 |
| D | 3.0 | 120.14 | 128.24 |

*Storage at 50° C.

Formula With Titanium Dioxide

| Sample | CLA Content (%) | % Viscosity Change 1 month |
|---|---|---|
| A | 0 | −29.47 |
| B | 1.0 | −27.69 |
| C | 2.0 | −17.04 |
| D | 3.0 | −6.51 |

*Storage at 50° C.

The formulas with zinc oxide exhibited an increased viscosity change with the addition of small amounts of CLA. By contrast, replacement of zinc oxide with titanium dioxide decreased viscosity but only to a relatively small extent. As CLA increased from 1% to 3%, the viscosity change became less. It is evident that CLA is effective in stabilizing formulas with titanium dioxide in an oil continuous system.

What is claimed is:

1. A cosmetic composition which is a water-in-oil emulsion comprising:
   (i) from about 0.1 to about 30% by weight of a water-in-oil emulsifying silicone surfactant;
   (ii) from about 0.1 to about 30% by weight of a titanium dioxide sunscreen agent; and
   (iii) from about 0.1 to about 10% of a conjugated linoleic acid.

2. The composition according to claim 1 wherein the water-in-oil surfactant is a silicone copolyol.

3. The composition according to claim 1 wherein the titanium dioxide is present in an amount from about 1 to about 10% by weight of the composition.

4. The composition according to claim 1 wherein the conjugated linoleic acid is present in an amount from about 1 to about 3% by weight of the composition.

5. The composition according to claim 1 wherein the conjugated linoleic acid consists essentially of at least 30% by weight of total conjugated linoleic acid present in the composition of a mixture of cis-9, trans-11 and trans-10, cis-12 linoleic acids.

6. The composition according to claim 5 wherein the conjugated linoleic acid consists essentially of at least 40% by weight of total conjugated linoleic acid present in the composition of a mixture of cis-9, trans-11 and trans-10, cis-12 linoleic acids.

7. The composition according to claim 1 wherein the titanium dioxide has a particle size ranging from about 5 to about 100 nm.

8. The composition according to claim 1 wherein the titanium dioxide has a particle size ranging from about 10 to about 60 nm.

9. The composition according to claim 1 wherein the titanium dioxide is a oil dispersible titanium dioxide.

* * * * *

UNITED STATES PATENT AND TRADEMARK OFFICE
CERTIFICATE OF CORRECTION

PATENT NO. : 7,175,835 B1 Page 1 of 1
APPLICATION NO. : 11/318130
DATED : February 13, 2007
INVENTOR(S) : Simoulidis et al.

It is certified that error appears in the above-identified patent and that said Letters Patent is hereby corrected as shown below:

On the title page

Item 73

Conopco, Inc., Englewood Cliffs, NJ    should read

Conopco, Inc. d/b/a Unilever, Englewood Cliffs, NJ

Signed and Sealed this

Seventeenth Day of April, 2007

JON W. DUDAS
*Director of the United States Patent and Trademark Office*